United States Patent [19]

Schaefer et al.

[11] Patent Number: 4,833,225

[45] Date of Patent: May 23, 1989

[54] POLYQUATERNARY POLYSILOXANE POLYMERS, THEIR SYNTHESIS AND USE IN COSMETIC PREPARATIONS

[75] Inventors: Dietmar Schaefer; Manfred Krakenberg, both of Essen, Fed. Rep. of Germany

[73] Assignee: Th. Goldschdidt AG, Essen, Fed. Rep. of Germany

[21] Appl. No.: 154,964

[22] Filed: Feb. 10, 1988

[30] Foreign Application Priority Data

Feb. 18, 1987 [DE] Fed. Rep. of Germany ....... 3705121

[51] Int. Cl.$^4$ .............................................. C08G 77/04
[52] U.S. Cl. ........................................ 528/28; 528/31; 528/34; 528/40; 556/424; 556/425; 424/70
[58] Field of Search ...................... 528/28, 31, 34, 40; 556/424, 425

[56] References Cited

U.S. PATENT DOCUMENTS 4,533,714 8/1985 Sebag et al. ........................... 528/28

*Primary Examiner*—Melvyn I. Marquis
*Attorney, Agent, or Firm*—Toren, McGeady & Associates

[57] ABSTRACT

Polyquaternary polysiloxane polymers are disclosed comprising repeating units of

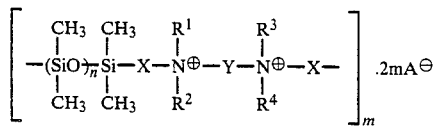

wherein X is a bivalent hydrocarbon group with at least 4 carbon atoms, which has a hydroxyl group and may be interrupted by an oxygen atom, Y is a bivalent hydrocarbon group with at least 2 carbon atoms, which has a hydroxyl group and which may be interrupted by an oxygen or nitrogen atom, $R^1$, $R^2$, $R^3$, $R^4$ are the same or different and may be alkyl groups with at least 1 to 4 carbon atoms or benzyl groups or in which $R^1$ and $R^3$ or $R^2$ and $R^4$ may be components of a bridging alkylene group, $A^{\ominus}$ is an inorganic or organic anion, n=5 to 200 m is a whole number $\geq 1$.

The compounds may be synthesized by an addition reaction between $\alpha,\omega$-hydrogenpolysiloxane of the formula

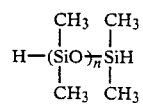

and epoxides which have a terminal olefinic bond and reacting the product obtained with a diamine of the general formula

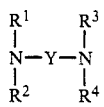

The polymers may be used in cosmetic preparations, especially in hair cosmetics. They improve the ability to comb the hair wet and dry, increase the gloss and reduce the electrostatic charge on the treated hair.

13 Claims, No Drawings

POLYQUATERNARY POLYSILOXANE POLYMERS, THEIR SYNTHESIS AND USE IN COSMETIC PREPARATIONS

FIELD OF INVENTION

The invention relates to novel polyquaternary polysiloxane polymers and methods for the synthesis of these compounds. It furthermore relates to the use of these polymers in cosmetic preparations.

BACKGROUND INFORMATION AND PRIOR ART

The use of organopolysiloxanes for the preparation of hair tonics and other hair care preparations is well known. In "Chemie und Technologie der Silicone" (Chemistry and Technology of the Silicones), by Walter Noll, Verlag Chemie, 2nd edition, 1968, page 536, however, it is stated that the objective of maintaining the hairdo independent of the effects of moisture cannot be accomplished with normal polydimethylsiloxanols. Rather, the silicone must be fixed on the hair with the help of functional groups.

German Auslegeschrift No. 1,493,384, discloses organosiloxane compounds or compound mixtures of the formula

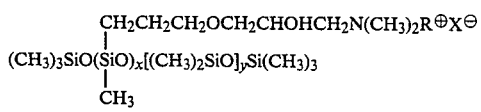

in which R represents hydrogen or $CH_3$, X is halogen and $x=1$ to 10 and $y=0$ to 8.5, y:x not being larger than 8.5:1.

These organosiloxanes with quaternary ammonium groups can be synthesized by reacting epoxysiloxanes of the formula

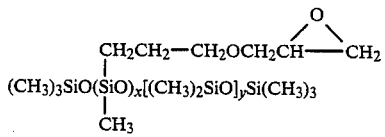

in a known manner with dimethylamine and converting the resulting dimethylaminoorganosiloxane of formula

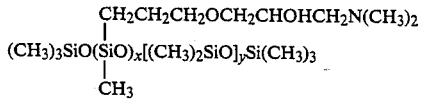

in a known manner with a hydrogen halide or with a methyl halide into the quaternary ammonium compound of the aforementioned formula.

According to U.S. Pat. No. 4,185,087, the aforementioned organopolysiloxanes with quaternary ammonium groups can be used for hair care preparations. It is stated in the patent that while simple, aqueous shampoos can release dirt and remove an excess of fat from the hair, most shampoos however remove fat so thoroughly from the hair that damage to the hair can be observed. The patent asserts that after being washed, the hair becomes electrostatically charged and therefore difficult to comb.

The patent also teaches that the addition of lanolin derivatives, glycol, fatty acid esters or proteins improves the manageability of the hair after washing. At the same time, however, the additions interfere with foaming during washing. The hair, pursuant to the patent, becomes somewhat sticky and does not feel natural.

The additions do not improve the ability to comb the washed hair, the stability of the hairdo and the gloss of the hair.

The starting materials for the preparation of the compounds described in the German Auslegeschrift No. 1,493,384 are the corresponding methylhydrogenpolysiloxanes. These generally are equilibrated mixtures, that is, siloxane mixtures, in which the number of methylhydrogensiloxy and dimethylsiloxy units corresponds to a random (statistical) distribution. Therefore, in siloxanes in which x has a low value, the proportion of such siloxanes in which $x=0$ cannot be disregarded. This means in turn that a proportion of unmodified silicone oils is unavoidably present in products of this method. This proportion, however, does not contribute to improving the ability to comb the hair or to improving the hairdo or the gloss of the hair.

It is a further disadvantage of the compounds described in the German Auslegeschrift No. 1,493,384 that the dimethylsiloxy chains are always interrupted by methylsiloxy groups which have lateral quaternary nitrogen groups. The typical siloxane character which is desirable for improving the properties of the hair, is, however, based particularly on the presence of dimethylsiloxy chains. The optimum ability to comb the hair and the optimum gloss are therefore not assured.

Similar teachings arise out of the European Pat. No. 0,017,121 (corresponding to the German Offenlegungsschrift No. 2,912,485). Here also, organopolysiloxanes with quaternary ammonium groups are described in shampoos and hair care preparations to improve the properties of the hair. The compounds correspond to the general formula

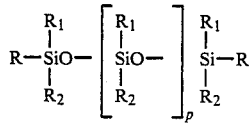

in which $R_1$ and $R_2$ represent alkyl groups with 1 to 4 carbon atoms or an aryl group, p represents the numbers from 0 to 50 and R the

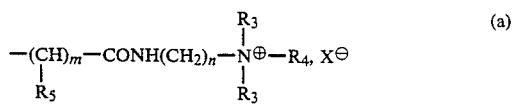 (a)

group or the

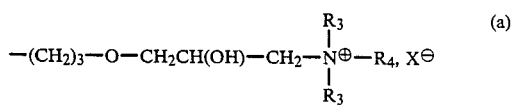 (a)

group, in which $R_3$ is an alkyl or hydroxyalkyl group with 1 to 3 carbon atoms, $R_4$ is $R_3$ or aryl—$CH_2$— or the allyl group, $R_5$ is hydrogen or methyl, $X^\ominus$ represents the anions $Cl^\ominus$, $Br^\ominus$, $I^\ominus$, $CH_3SO_4^\ominus$ or $C_2H_5SO_4^{\ominus}$, m represents numbers from 2 to 10 and n the numbers from 2 to 4.

It is a disadvantage of these compounds that, for small values of p, to wit with relatively low molecular weights, they can easily be washed out, since the organic character of the compounds predominates and their substantivity is slight. At high molecular weights, the properties of the dimethylsiloxy units increasingly predominate, while the influence of the quaternary ammonium groups decreases. In view of the desired application properties, it is therefore necessary to adhere to a relatively narrow molecular weight range if the balance of desired properties is to be assured.

German Offenlegungsschrift No. 3,340,708 discloses polyquaternary polysiloxane polymers which essentially consist of the following, recurring units of the general formula

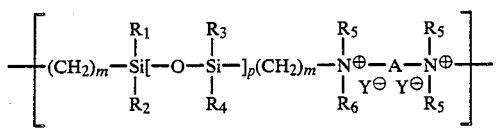

wherein

A is an $\alpha,\omega$-bis-alkoxypolysiloxane group or a linear or branched, saturated or unsaturated hydrocarbon chain which contains up to 6 consecutive carbon atoms and which has one or several hydroxy group(s) and may be interrupted by one or several oxygen atom(s) and/or by one or several aromatic ring(s);

$R_1$, $R_2$, $R_3$ and $R_4$ may be the same or different and represent a $C_{1-6}$ alkyl group or a phenyl group;

$R_5$ is a methyl, ethyl or hydroxyethyl group;

$R_6$ is a $C_{1-18}$ alkyl group or a bivalent —$CH_2$— group. In the latter case the two $R_6$ groups are joined to each other and, together with the two nitrogen atoms and the A group, which represents a —$CH_2$—$CH_2$— group, form a bivalent piperazino group;

or the $R_5$ and $R_6$ groups, each represent a —$CH_2$ group and, together with the two nitrogen atoms and the A group, which represents a $CH_2$—$CH_2$ group, form a bivalent triethylenediamino group;

or the $R_5$ and $R_6$ are joined together and, together with the nitrogen atom to which they are linked, form a heterocyclic compound, such as, for example, a compound with a piperidine, morpholine or pyrrolidine ring;

$Y^-$ represents a $Cl^-$—, $Br^-$—, $CH_3SO_3^-$— or

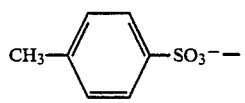

anion m is a whole number from 1 to 6 and p is a whole number or a decimal number from 1 to 50.

Polyquaternary polysiloxane polymers of this type do not have the above described disadvantages of compounds of the German Offenlegungsschrift No. 2,912,485. The practical use of these compounds is, however, opposed by their complicated manufacturing method which requires considerable expenditure. The compounds can be synthesized in yields of $\leq 60\%$ of the theoretical, which cannot be justified economically.

Finally, reference is made to the published European patent application No. 0,095,238, which is directed to a composition having essentially the following components:

(A) a siloxane of the general formula

in which R is described only by its purpose as a functional group which brings about adhesion to the hair, such as an amino, carboxylic acid or quaternary ammonium group. X is hydrogen or a phenyl, hydroxyl or saturated hydrocarbon group with 1 to 8 carbon atoms, a has a value of 0 to 3, b has a value of 0 to 1 and n+m has a value of 1 to 1999, n having a value of from 0 to 2000 and m having a value of from 1 to 2000, (B) a surfactant (C) an addition to improve the freeze/thaw stability and (D) water.

OBJECTS OF THE INVENTION

It is the primary object of the invention to provide polyquaternary polysiloxane polymers which can be synthesized in significantly higher yields than is possible according to the state of the art and moreover have the desired property profile which is given by the combination of the following properties: the treated hair can be combed well and has a pleasing gloss, the compounds have increased substantivity and, due to this, are not washed out as readily from the surface of the hair; the compounds have high antistatic effectiveness and good physiological compatibility with the hair and the scalp.

It is another object of the invention to provide for a process for synthesizing the novel polyquaternary polysiloxane polymers in a simple and expeditious manner and in a high yield.

It is also an object of the invention to provide cosmetic preparation, in particular hair care preparations of superior quality.

Generally, it is an object of the invention to improve on the art of polyquaternary polysiloxane polymers, the methods of their preparation as well as their use in cosmetic preparations.

SUMMARY OF THE INVENTION

Surprisingly, it has been ascertained that these properties are found in polyquaternary polysiloxane polymers which consist essentially of the following repeating units

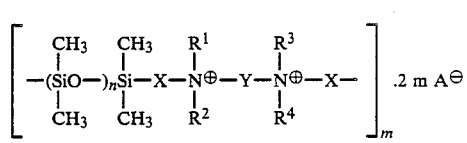

wherein

X is a bivalent hydrocarbon group with at least 4 carbon atoms which has a hydroxyl group and may be interrupted by an oxygen atom, Y is a bivalent hydrocarbon group with at least 2 carbon atoms which has a hydroxyl group and which may be interrupted by an oxygen or nitrogen atom, $R^1$, $R^2$, $R^3$, $R^4$ are the same or different and are alkyl groups with at least 1 to 4 carbon atoms or benzyl groups or in which $R^1$ and $R^3$ or $R^2$ and $R^4$ may be components of a bridging alkylene group, A is an inorganic or organic anion,
n=5 to 200
m is a whole number ≧1.

The structure of the polymers is of the AB type, the A block being represented by the formula

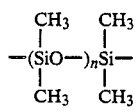

and the B block by the formula

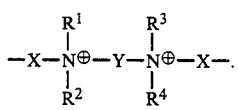

It is a special advantage of polymers of this type that, for a given ratio of the A blocks to the B blocks, the molecular weight can be adjusted practically at will without changing the ratio of dimethylsiloxy units to the number of units with quaternary nitrogen atoms. This is of importance because a number of properties related to the application, such as the viscosity of the solutions of the polymers, their hair care properties as well as other properties, depend on the molecular weight and products with a higher molecular weight are desirable especially in cosmetic products.

No terminal groups are indicated in the general formula I. No such groups are present if the polymers are present in cyclic form. If the polymers have a linear structure, then the nature of the terminal groups is determined by the method employed for their synthesis. Linear polymers may be represented by the general formula

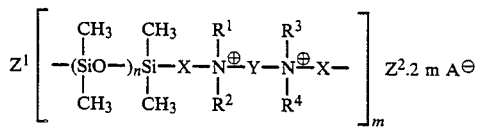

$Z^1$ may be H, OH, an alkyl or an alkoxy group.

$Z^1$ may also be a hydrocarbon group with at least 4 carbon atoms, which has one or several hydroxyl group(s) and may be interrupted by one or several oxygen atoms.

$Z^1$ may also represent the following group:

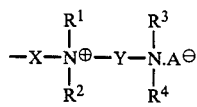

Finally, $Z^1$ may also represent the group

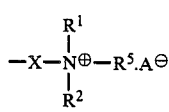

wherein $R^5$ is an alkyl group with 1 to 20 carbon atoms.

Examples of the $Z^1$ terminal groups are

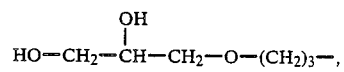

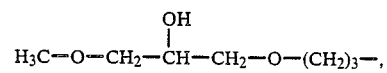

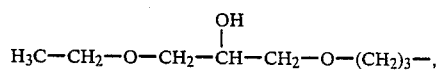

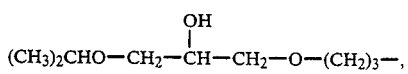

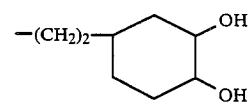

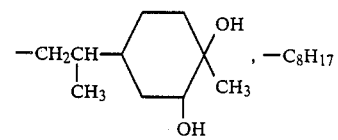

$Z^2$ may represent the following group:

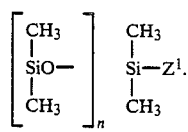

In Formula I, X is a bivalent hydrocarbon group with at least 4 carbon atoms, which has a hydroxyl group and which may be interrupted by an oxygen atom. Preferably, the bivalent hydrocarbon group has 4 to 10 carbon atoms. The following groups are especially preferred.

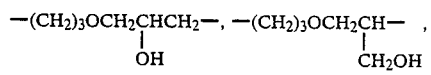

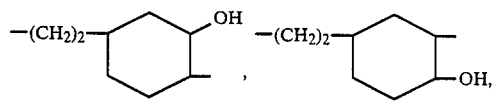

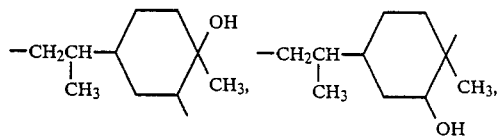

Examples of further X groups are:

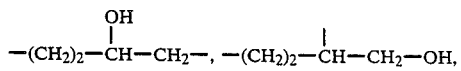

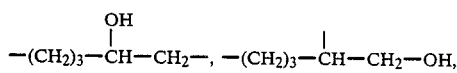

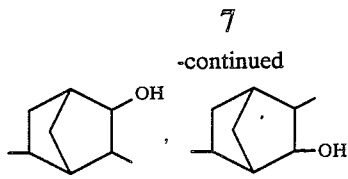

Y is a bivalent hydrocarbon group with at least 2 carbon atoms, which has a hydroxyl group and which may be interrupted by an oxygen or nitrogen atom. Preferred are bivalent hydrocarbon groups with 2 to 6 carbon atoms, especially groups of the formula $-(CH_2)_o-$, in which o is 2 to 6.

Further Examples of suitable Y groups are

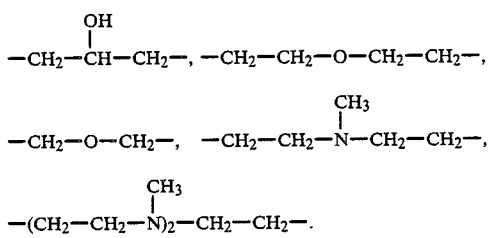

The $R^1$, $R^2$, $R^3$ and $R^4$ may be the same or different and may represent alkyl groups with 1 to 4 carbon atoms or benzyl groups. The $R^1$ and $R^3$ groups as well as the $R^2$ and $R^4$ groups may be components of a bridging alkylene group. Polymer block B may assume the following structure:

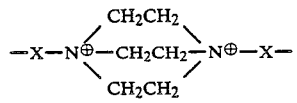

Preferably, $R^1$, $R^2$, $R^3$ and $R^4$ are methyl groups.

$A^\ominus$ is any inorganic or organic anion. When using the new polymers of the invention as a component of hair care preparations, care must be taken to ensure that the anion originates from a physiologically compatible acid. Examples of suitable anions are acetate, chloride, bromide, hydrogen sulfate and sulfate anions.

n defines the number of dimethylsiloxy units in Block A and is a number between 5 and 200. Since the given Formula I is a general formula, the numerical values represent average values.

m defines the number of polymer blocks AB and is equal to or greater than 1.

Examples of polymers of the invention are:

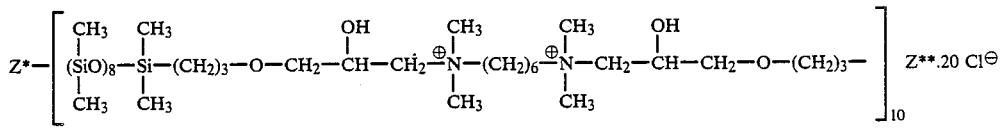

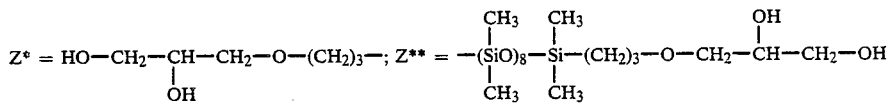

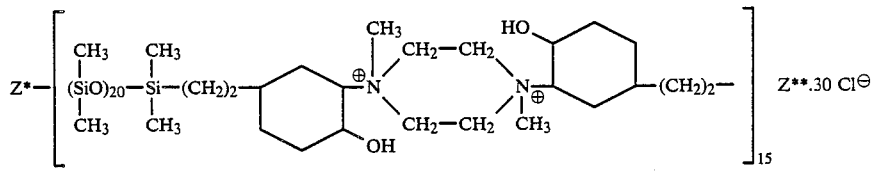

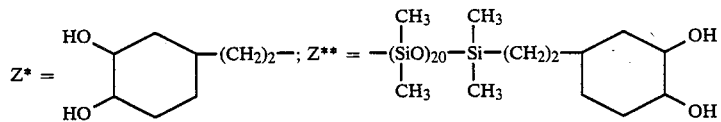

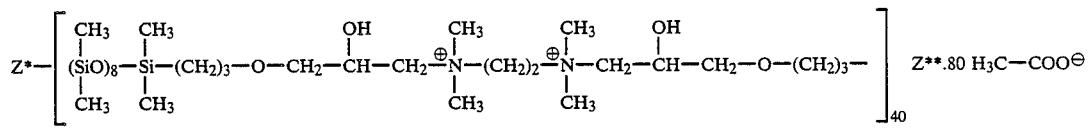

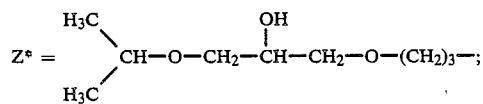

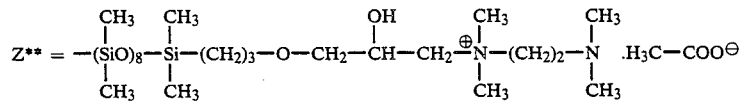

-continued

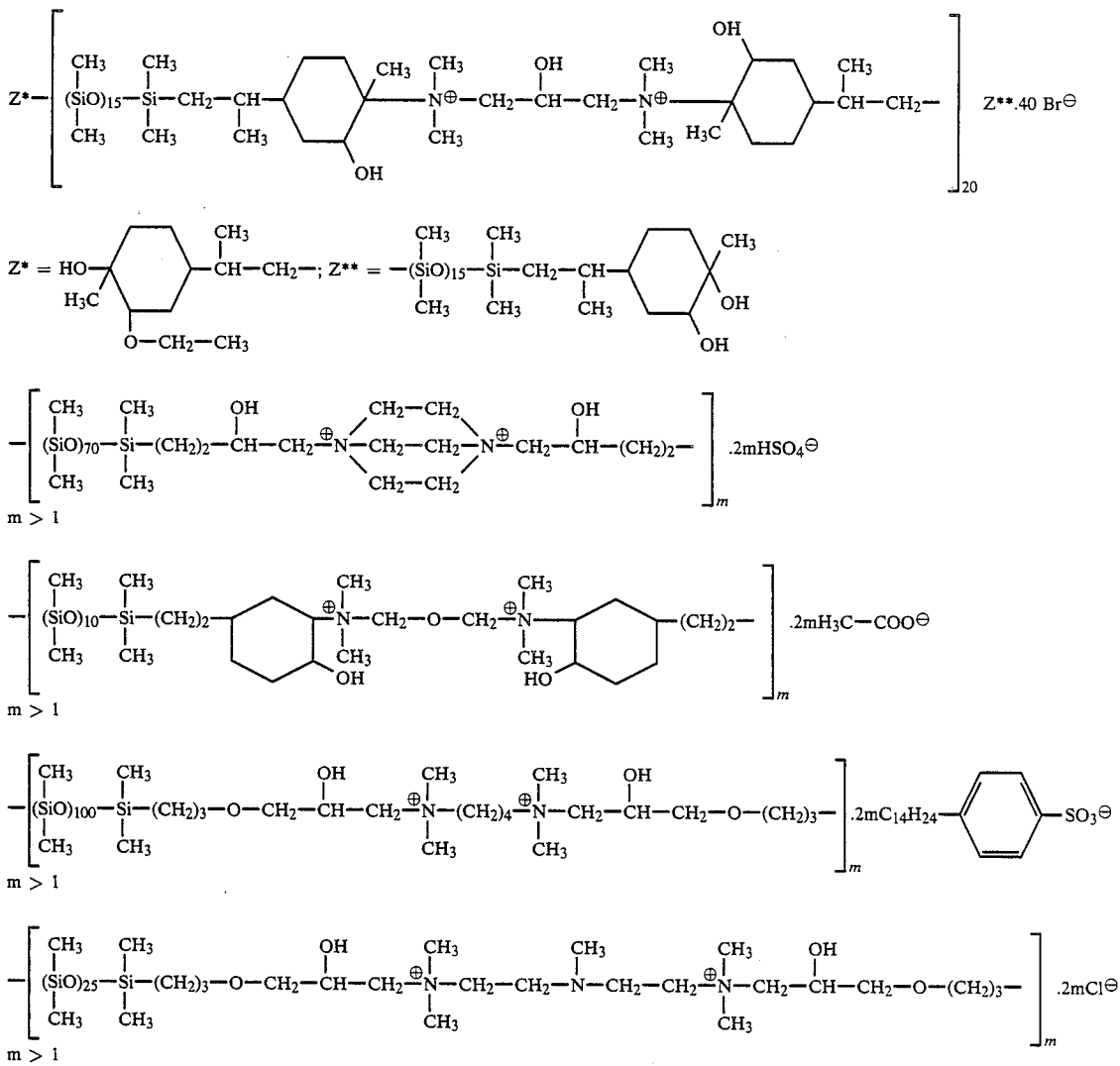

The products of the invention are viscous to highly viscous, oily to pasty, colorless to slightly yellowish to reddish products. The solubility of the polymers of the invention is determined by the ratio of dimethylsiloxy units to the number of quaternary ammonium groups and by the molecular weight of the compounds.

For use in cosmetics, especially in hair preparations, products are generally preferred which are soluble in water or in water-miscible auxiliary solvents, such as monohydric or polyhydric alcohols.

A further aspect of the present invention is the synthesis of the compounds of the invention. The method pursuant to the invention is characterized in that α,ω-hydrogenpolysiloxanes of the general formula

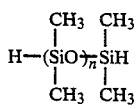

are first reacted with, based on the SiH groups, equimolar amounts of an epoxide, which has a terminal olefinic bond, the epoxide having at least 4 carbon atoms and possibly a noncyclic ether group as well. The reaction is carried out in the presence of a hydrosilylating catalyst at temperatures of 50° to 150° C. in a known manner and the reaction product, so obtained, is reacted with a ditertiary diamine of the general formula

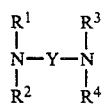

in the presence of 2 mole equivalents of acid HA, based on the diamine, at temperatures of 40° to 120° C. in such amounts that for each epoxide group, there is a corresponding tertiary amine group.

The method of the invention proceeds in a known manner. The method starts out with hydrogenpolysiloxanes with terminal SiH groups. The number of dimethylsiloxy units is selected according to the desired end product. Equimolar amounts of an epoxide are now added on the terminal SiH groups of the hydrogenpolysiloxanes, the epoxide having a terminal olefinic double bond and at least 4 carbon atoms and may also comprise a noncyclic ether group. The addition reaction of the terminal olefinic, unsaturated group with the SiH group takes place in the presence of a hydrosilylating catalyst at temperatures from 50° to 150° C. As hydrosilylating catalyst, platinum catalysts may be used, which are known for such a reaction, for example, hexachloroplatinic acid or cis-dichlorodiamino platinum.

Preferably, compounds having the formula

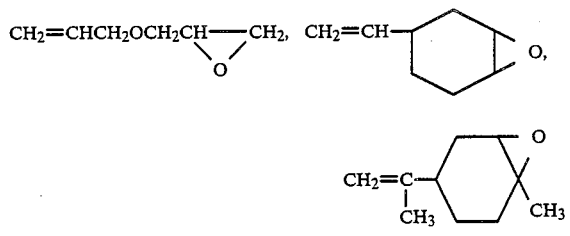

are used as epoxides with a terminal olefinic group.

This first step of the reaction is illustrated by the following equation:

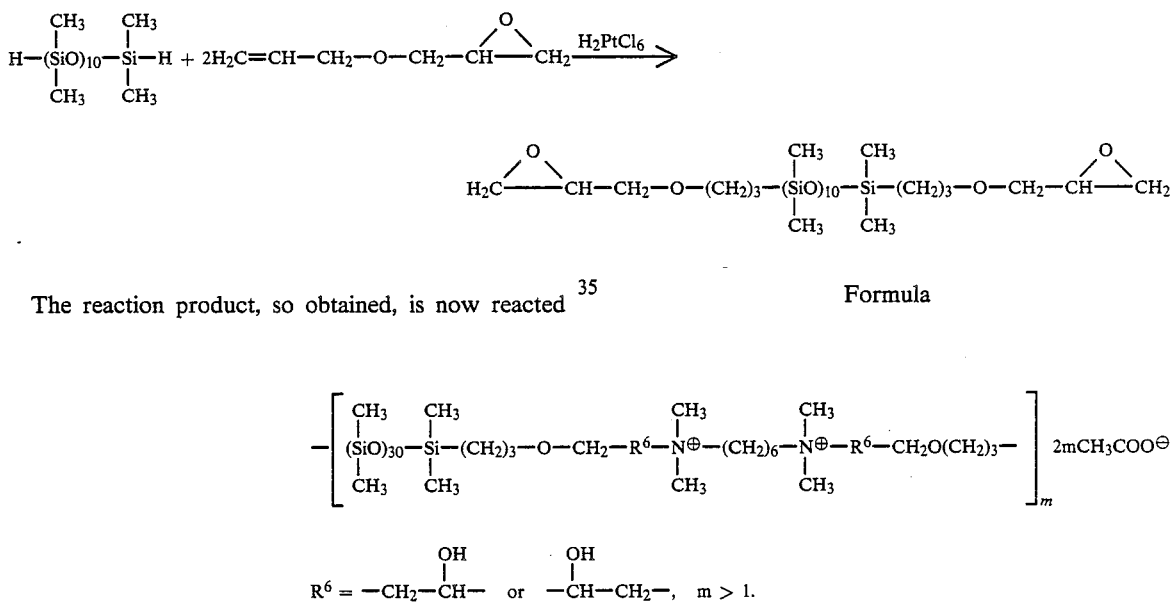

The reaction product, so obtained, is now reacted with a ditertiary diamine of the general formula

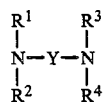

in the presence of 2 mole equivalents of the acid HA, based on the diamine, at temperatures of 40° to 120° C. in such amounts, that each epoxide group corresponds to a tertiary amine group.

Preferably, compounds of the formula

in which o is 2 to 6, are used as ditertiary diamines.

The first step of the 2-step synthesis method is preferably carried out without the use of a solvent. The second step of the reaction is preferably carried out in an aqueous or aqueous alcoholic solution. The maximum temperature of the reaction of the second step therefore is generally determined by the refluxing temperature of the solvent used. It should, however, not exceed 120° C.

The yields of the method of the invention generally are at least 90% and mostly even 95% of the theoretical; in some cases, they are even higher.

A further aspect of the invention is the use of the compounds of the invention in cosmetics, especially, as explained in the use of the compounds in preparations for the care of hair. The compounds of the invention have the required combination of properties as listed above.

Methods for the synthesis of the compounds of the invention as well as their properties are described in greater detail in the following examples, it being understood that these examples are given by way of illustration and not by way of limitation.

EXAMPLE 1

Synthesis of a Polymer of the Invention of the General Formula

In a 0.5 L 4-neck flask, equipped with stirrer, dropping funnel, thermometer and reflux condenser, 30 g (0.26 moles) of allyl glycidyl ether are heated together with 0.022 g (7.4×10$^{-5}$ moles) of (NH$_3$)$_2$PtCl$_2$ under a nitrogen atmosphere to a temperature of 115° C. Within a period of 15 minutes, 228 g (0.1 mole) of an α,ω hydrogensiloxane of the general formula

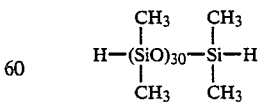

are added dropwise to this mixture. The reaction mixture is stirred for a further 3 hours at 115° C. Subsequently, the excess allyl glycidyl ether is distilled off at 0.2 bar and 100° C.

An α,ω-diepoxysiloxane (246 g, 0.098 moles, 98%) of the general formula

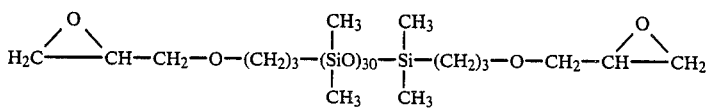

is obtained. For the further reaction, 14.1 g (0.098 moles) of N,N,N',N'-tetramethyl-1,4-butanediamine together with 40 g of water are added to a 1 L 4-neck flask, which is equipped with a stirrer, dropping funnel, thermometer and reflux condenser, and mixed at 20° C. with 12 g (0.2 moles) of acetic acid. After 30 minutes, the temperature is raised to 50° C. and the α,ω-diepoxysiloxane, obtained above, is added dropwise. After the addition of 100 mL of isopropanol, the mixture is heated to the refluxing temperature and stirred for 6 hours. The water/isopropanol mixture is distilled off at 100° C. and 0.2 bar.

The polyquaternary polysiloxane polymer (268 g) is obtained as a yellow to reddish product, which barely can flow at room temperature. Quaternary nitrogen: found 0.9%; calc. 1.0%

EXAMPLE 2

Synthesis of a Polymer of the General Formula:

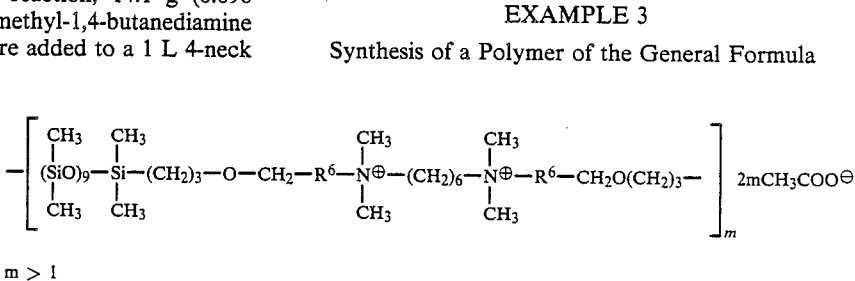

m > 1

The method is similar to that described in Example 1, N,N,N',N'-tetramethyl-1,6-hexanediamine being used instead of N,N,N',N'-tetramethyl-1,4-butanediamine.

Formulation

| | |
|---|---|
| N,N,N'—tetramethyl-1,6-hexanediamine: | 16.8 g (0.098 moles) |
| acetic acid: | 12 g (0.2 moles) |
| α,ω-diepoxysiloxane from Example 1: | 245 g (0.098 moles |
| water: | 40 g |
| isopropanol: | 100 g |

A polyquaternary polysiloxane polymer (272 g) is obtained as a yellow to reddish product, which is barely able to flow at room temperature Quaternary nitrogen: found 1.0%; calc. 1.0%

EXAMPLE 3

Synthesis of a Polymer of the General Formula

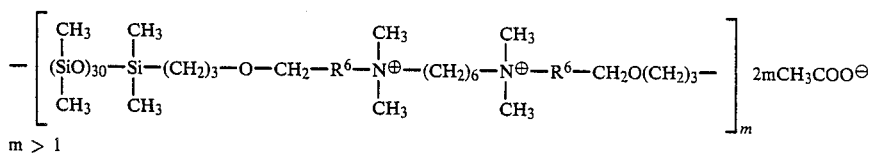

m > 1

In a 0.5 L 4-neck flask, equipped with stirrer, dropping funnel, thermometer and reflux condenser, 57 g (0.5 moles) of allyl glycidyl ether are heated together with 0.022 g (7.4×10⁻⁵ moles) of (NH₃)₂PtCl₂ under an atmosphere of nitrogen to 115° C. Within 15 minutes, 145 g (0.2 moles) of an α,ω-hydrogen siloxane of the general formula

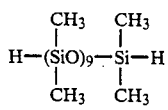

are added dropwise to this. The reaction mixture is stirred for a further 3 hours at 115° C. Subsequently, the excess allyl glycidyl ether is distilled off at 0.2 bar and 100° C.

An α,ω-diepoxysiloxane (182 g, 0.19 moles, 95%) of the general formula

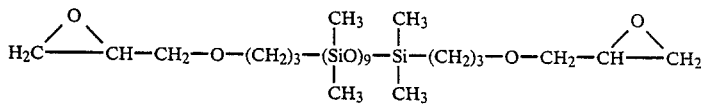

is obtained. For the further reaction, 32.7 g (0.19 moles) of N,N,N',N'-tetramethyl-1,6-butanediamine and 40 g of water are added to a 1 L 4-neck flask, which is equipped with a stirrer, dropping funnel, thermometer and reflux condenser, and treated with 24 g (0.4 moles) of acetic acid. After 30 minutes, the temperature is raised to 50° C. and the above-obtained α,ω-diepoxysiloxane is added dropwise. After the addition of 100 mL of isopropanol, the mixture is heated to the refluxing temperature and stirred for 5 hours. The water/isopropanol mixture is distilled off at 100° C. and 0.2 bar.

A polyquaternary polysiloxane polymer (236 g) is obtained as a yellow to reddish product, which can barely flow at room temperature. Quaternary nitrogen: found 2.2%, calc. 2.2%.

EXAMPLE 4

Preparation and Testing of Hair Care Preparations, Using the Polyquaternary Polysiloxane Polymers (Percentages are by Weight), Synthesized in Examples 1 to 3.

| Conditioning Shampoo I | | Composition | Condition shampoo II | |
|---|---|---|---|---|
| A< | Tego ® betaine L 7[1] | 2% | Tego ® betaine L 7[1] | 3% |
|  | ANTIL ® 141 LIQUID[2] | 3% | ANTIL ® 141 LIQUID[2] | 3% |
| B< | polyquat from Example 1 | 2% | polyquat from Example 2 | 2% |
|  | 1,2-propyleneglycol | 4% | 1,2-propyleneglycol | 4% |
| C | sodium lauryl ether sulfate | 10% | triethanolamine lauryl sulfate | 12% |
| E | sodium chloride | 3.5% | sodium chloride | — |
| D | water | 75.5% | water | 76% |

[1]Tego ® betaine L 7 = cocamidopropyl betaine (1-alkylamino-3-dimethylammonium-propane-3-carboxymethyl-betaine).
[2]ANTIL ® 141 LIQUID is a liquid thickner, the basis of which is a nonionic fatty acid polyalkyleneglycol ester.

For the preparation, the components are added together in the order listed (A to E). Each mixture has to form a clear solution before further components are added.

| Cream Rinse | | |
|---|---|---|
| A< | TEGINACID ® X[3] | 6% |
|  | cetyl alcohol | 0.5% |
| B< | polyquat from Example 3 | 2% |
|  | water | 91.5% |

[3]TEGINACID ® X is an o/w emulsifier, the basis of which is a mixture of glycerin monostearates with ployglycol fatty alcohol ethers.

For the preparation, A and B are mixed together, homogenized and cooled with stirring.

In a practical application in a side-by-side comparison test (one-half of the hair with inventive product and the other half prior art product) on human hair, the ability to comb wet and dry hair was better, the gloss was improved and the electrostatic charge on the treated hair was less in comparison with shampoo formulations or cream rinses with polyquaternary siloxanes of the state of the art and conditioning shampoos and cream rinses on the market which are based on a strictly organic polyquat.

We claim:
1. A polyquaternary polysiloxane polymer, consisting essentially of repeating units of

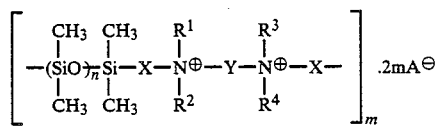

wherein
X is selected from the group consisting of a bivalent hydrocarbon group with at least 4 carbon atoms and containing a hydroxyl group and a bivalent hydrocarbon group with at least 4 carbon atoms interrupted by an oxygen atom and containing a hydroxyl group, X bridging an Si-atom with a nitrogen atom;
Y is selected from the group consisting of a bivalent hydrocarbon group with at least 2 carbon atoms, a bivalent hydrocarbon group with at least 2 carbon atoms interrupted by an oxygen atom or a nitrogen atom, and a bivalent hydrocarbon group with at least 2 carbon groups and containing a hydroxyl group, Y bridging 2 nitrogen atoms;
$R^1$, $R^2$, $R^3$, $R^4$ are the same or different and are alkyl groups with at least 1 to 4 carbon atoms or benzyl groups or $R^1$ and $R^3$ on the one hand or $R^2$ and $R^4$ on the other are components of an alkylene group,
$A^\ominus$ is an inorganic or organic anion,
n = 5 to 200
m is a whole number $\geq 1$.

2. The polymer of claim 1, wherein X is a

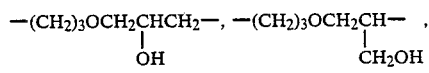

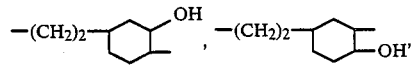

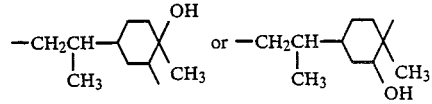

group.

3. The polymer of claim 1, wherein X is a

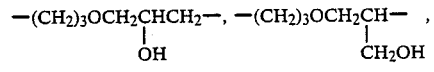

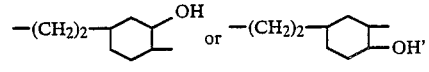

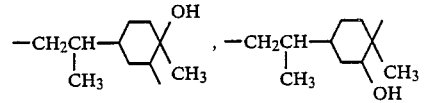

group.

4. The polymer of claim 1, wherein Y is a —$(CH_2)_o$— group, in which o is 2 to 6.

5. The polymer of claim 1, wherein $R^1$, $R^2$, $R^3$ and $R^4$ are methyl groups.

6. The polymer of claim 1, wherein the polymer is in cyclic form.

7. The polymer of claim 1, wherein the polymer is in linear form and has the general formula

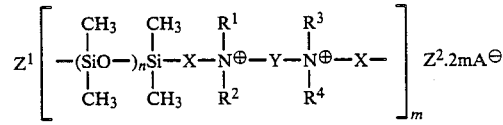

wherein X, Y, R¹, R², R³, R⁴, A⊖, n and m have the above meaning,

Z¹ is a terminal group selected from the group consisting of H, OH, alkyl, alkoxy, hydrocarbon with at least 4 carbon atoms comprising at least one hydroxyl group, the group

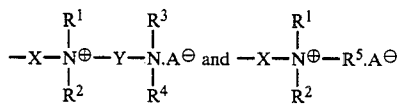

wherein R⁵ is alkyl with 1–20 carbon atoms and Z² is

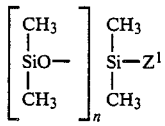

8. The polymer of claim 1, wherein X is a bivalent hydrocarbon with 4 to 10 carbon atoms.

9. A method of preparing a polyquaternary polysiloxane polymer of repeating units of

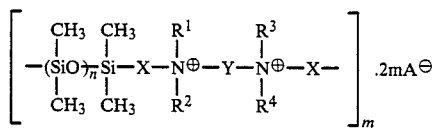

wherein

X is selected from the group consisting of a bivalent hydrocarbon group with at least 4 carbon atoms and containing a hydroxyl group and a bivalent hydrocarbon group with at least 4 carbon atoms interrupted by an oxygen atom and containing a hydroxyl group, X bridging an Si-atom with a nitrogen atom;

Y is a bivalent hydrocarbon group with at least 2 carbon atoms interrupted by an oxygen atom or a nitrogen atom, and a bivalent hydrocarbon group with at least 2 carbon groups and containing a hydroxyl group, Y bridging 2 nitrogen atoms;

R¹, R², R³, R⁴ are the same or different and are alkyl groups with at least 1 to 4 carbon atoms or benzyl groups or in which R¹ and R³ or R² and R⁴ are components of an alkylene group;

A⊖ is an inorganic or organic anion, n = 5 to 200 m is a whole number ≧ 1, said method comprising (a) reacting an α,ω-hydrogenpolysiloxane of the general formula

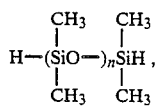

with, based on the SiH groups, equimolar amounts of an epoxide, having a terminal olefinic bond and at least 4 carbon atoms in the presence of a hydrosilylating catalyst at temperatures from 50° to 150° C., whereupon (b) the reaction product thus obtained is reacted with a ditertiary diamine of the general formula

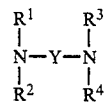

in the presence of 2 mole equivalents of HA acid, based on diamine, at temperatures of 40° to 120° C. and in such amounts that each epoxide group corresponds to a tertiary amine group.

10. The method of claim 9, wherein the epoxide contains a noncyclic ether group.

11. The method of claim 9, wherein the epoxide is

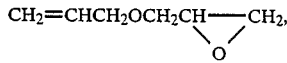

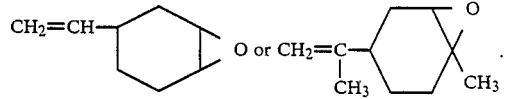

12. The method of claim 9 or 10, wherein said diamine of step (b) has the formula

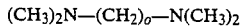

in which o is 2 to 6.

13. The method of claim 9 or 10, wherein step (b) is carried out in an aqueous or aqueous alcoholic solution.

* * * * *

UNITED STATES PATENT AND TRADEMARK OFFICE
CERTIFICATE OF CORRECTION

PATENT NO. : 4,833,225
DATED      : May 23, 1989
INVENTOR(S) : Dietmar Schaefer and Manfred Krakenberg It is certified that error appears in the above-identified patent and that said Letters Patent is hereby corrected as shown below:

Title page:

--[73]  Assignee:   Th. Goldschmidt AG, Essen,
                    Fed. Rep. of Germany--

Signed and Sealed this

Ninth Day of January, 1990

*Attest:*

JEFFREY M. SAMUELS

*Attesting Officer*       *Acting Commissioner of Patents and Trademarks*